United States Patent
Boylan et al.

(10) Patent No.: US 6,554,848 B2
(45) Date of Patent: Apr. 29, 2003

(54) MARKER DEVICE FOR ROTATIONALLY ORIENTING A STENT DELIVERY SYSTEM PRIOR TO DEPLOYING A CURVED SELF-EXPANDING STENT

(75) Inventors: John F. Boylan, Murrieta, CA (US); Benjamin C. Huter, Murrieta, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 95 days.

(21) Appl. No.: 09/796,183

(22) Filed: Feb. 27, 2001

(65) Prior Publication Data

US 2001/0049549 A1 Dec. 6, 2001

Related U.S. Application Data

(63) Continuation-in-part of application No. 09/586,211, filed on Jun. 2, 2000.

(51) Int. Cl.⁷ .............................. A61F 11/00; A61F 2/06
(52) U.S. Cl. ..................... 606/191; 623/1.15; 606/108
(58) Field of Search ................... 606/191, 192, 606/194, 195, 198, 197, 108; 623/1.19, 1.2, 1.18, 1.16, 1.15, 1.12; 607/122

(56) References Cited

U.S. PATENT DOCUMENTS

| | | |
|---|---|---|
| 4,505,767 A | 3/1985 | Quin |
| 4,580,568 A | 4/1986 | Gianturco |
| 4,665,906 A | 5/1987 | Jervis |
| 4,856,516 A | 8/1989 | Hillstead |
| 4,881,981 A | 11/1989 | Thoma et al. |
| 4,925,445 A | 5/1990 | Sakamoto et al. |
| 5,067,957 A | 11/1991 | Jervis |
| 5,092,877 A | 3/1992 | Pinchuk |
| 5,180,376 A | 1/1993 | Fischell |
| 5,190,546 A | 3/1993 | Jervis |
| 5,292,331 A | 3/1994 | Boneau |
| 5,458,615 A | 10/1995 | Klemm et al. |
| 5,476,505 A | 12/1995 | Limon |
| 5,484,425 A | 1/1996 | Fischell et al. |
| 5,485,667 A | 1/1996 | Kleshinski |
| 5,514,154 A | 5/1996 | Lau et al. |
| 5,562,641 A | 10/1996 | Flomenblit et al. |
| 5,569,295 A | 10/1996 | Lam |
| 5,597,378 A | 1/1997 | Jervis |
| 5,601,593 A * | 2/1997 | Freitag ............... 606/198 |
| 5,637,089 A | 6/1997 | Abrams et al. |
| 5,643,312 A | 7/1997 | Fischell et al. |
| 5,702,438 A * | 12/1997 | Aritall ............... 607/122 |
| 5,716,393 A | 2/1998 | Lindenberg et al. |
| 5,776,141 A | 7/1998 | Klein et al. |
| 5,779,731 A | 7/1998 | Leavitt |
| 5,824,037 A | 10/1998 | Fogarty et al. |
| 5,843,027 A | 12/1998 | Stone et al. |
| 5,843,244 A | 12/1998 | Pelton et al. |
| 5,879,370 A | 3/1999 | Fischell et al. |
| 5,885,381 A | 3/1999 | Mitose et al. |
| 5,907,893 A | 6/1999 | Zadno-Azizi et al. |
| 5,927,345 A | 7/1999 | Samson |

(List continued on next page.)

Primary Examiner—Gloria M. Hale
(74) Attorney, Agent, or Firm—Fulwider Patton Lee & Utecht, LLP

(57) ABSTRACT

A stent for use in a curved body lumen is disclosed. The stent is made from a superelastic alloy such as nickel titanium or nitinol, and optionally includes a ternary element. The superelastic alloy has a low temperature phase or martensitic phase and a high temperature phase or an austenitic phase. In the high temperature phase, the stent has a curve along the length that closely matches the curve of the vessel in the patient's anatomy. When deployed in the curved vessel of the patient, the heat set curve of the stent closely conforms to the curvature in the vessel and minimizes trauma and stress to the vessel.

20 Claims, 5 Drawing Sheets

U.S. PATENT DOCUMENTS

| | | |
|---|---|---|
| 6,042,605 A | 3/2000 | Martin et al. |
| 6,051,021 A | 4/2000 | Frid |
| 6,059,810 A | 5/2000 | Brown et al. |
| 6,077,295 A | 6/2000 | Limon et al. |
| 6,086,610 A | 7/2000 | Duerig et al. |
| 6,270,524 B1 * | 8/2001 | Kim .......................... 623/1.15 |
| 6,312,461 B1 * | 11/2001 | Unsworth et al. .......... 623/1.19 |
| 6,368,344 B1 * | 4/2002 | Fitz ............................ 623/1.11 |
| 6,371,962 B1 * | 4/2002 | Ellis et al. ................... 606/108 |
| 6,375,676 B1 * | 4/2002 | Cox ........................... 623/1.16 |
| 6,409,750 B1 * | 6/2002 | Hyodoh et al. .............. 623/1.1 |

\* cited by examiner

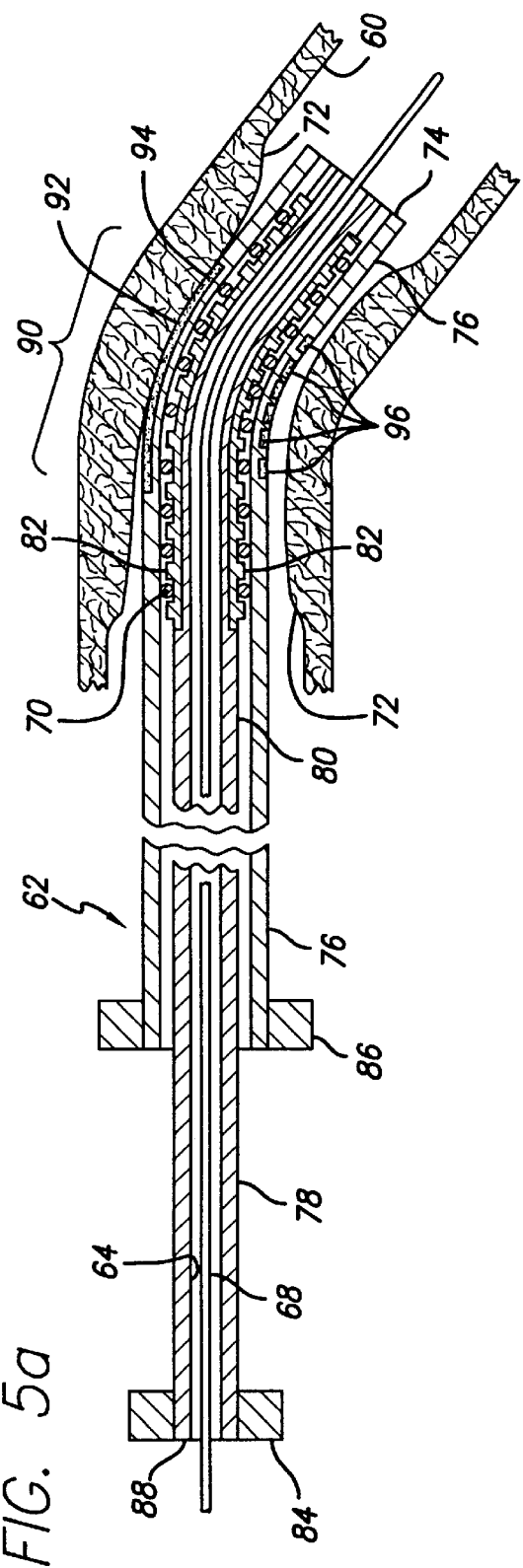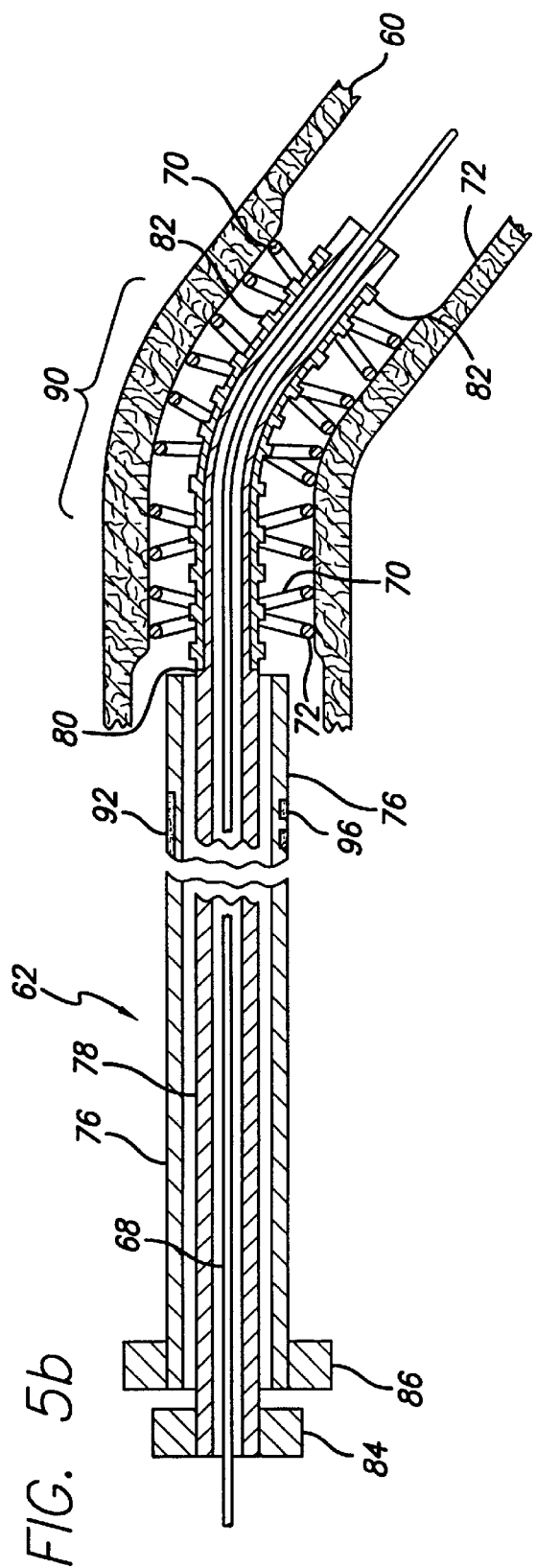

MARKER DEVICE FOR ROTATIONALLY ORIENTING A STENT DELIVERY SYSTEM PRIOR TO DEPLOYING A CURVED SELF-EXPANDING STENT

CROSS-REFERENCE TO RELATED APPLICATIONS

This application is a continuation-in-part of co-pending application having U.S. Ser. No. 09/586,211, filed Jun. 2, 2000, entitled "Curved Nitinol Stent For Extremely Tortuous Anatomy," the entire contents of which are hereby incorporated by reference.

BACKGROUND OF THE INVENTION

The present invention generally relates to self-expanding endoprosthetic devices. In particular, the present invention relates to self-expanding, intraluminal, vascular grafts, generally called stents, adapted to be implanted in a body lumen, such as carotid arteries, coronary arteries, peripheral arteries, veins, or other vessels to maintain the patency of the lumen.

These devices are frequently used in the treatment of atherosclerotic stenosis in blood vessels especially after percutaneous transluminal angioplasty (PTA) or percutaneous transluminal coronary angioplasty (PTCA) procedures, with the intent to reduce the likelihood of restenosis of a vessel. Stents are also used to support a body lumen, tack-up a flap or dissection in a vessel, or in general where the lumen is weak to add support.

For example, during PTCA procedures, it is common to use a dilation catheter to expand a diseased and partially occluded coronary artery so that blood freely flows. Despite the beneficial aspects of PTCA procedures and its widespread and accepted use, it has several drawbacks, including the possible development of restenosis and perhaps acute thrombosis and sub-acute closure. This recurrent stenosis has been estimated to occur in seventeen to fifty percent of patients despite the initial PTCA procedure being successful. Restenosis is a complex and not fully understood biological response to injury of a vessel which results in chronic hyperplasia of the neointima. This neointimal hyperplasia is activated by growth factors which are released in response to injury. Acute thrombosis is also a result of vascular injury and requires systemic antithrombotic drugs and possibly thrombolytics as well. This therapy can increase bleeding complications at the catheter insertion site and may result in a longer hospital stay. Sub-acute closure is a result of thrombosis, elastic recoil, and/or vessel dissection.

Several procedures have been developed to combat restenosis and sub-acute or abrupt closure, one of which is the delivery and implantation of an intravascular stent. Stents are widely used throughout the United States and in Europe and other countries. Generally speaking, the stents can take numerous forms, however, most common is a generally cylindrical hollow tube that holds open the vascular wall at the area that has been dilated by a dilation catheter. One highly regarded stent used and sold in the United States is marketed under the tradename ACS Multi-Link Stent, which is made by Advanced Cardiovascular Systems, Inc., Santa Clara, Calif.

For expandable stents that are delivered with expandable catheters, such as balloon catheters, the stents are positioned over the balloon portion of the catheter and are expanded from a reduced delivery diameter to an enlarged deployment diameter greater than or equal to the inner diameter of the arterial wall by inflating the balloon. Stents of this type are expanded to an enlarged diameter through deformation of the stent, which then engages the vessel wall. Eventual endothelial growth of the vessel wall covers over the stent.

Other stents are self-expanding where the expansion occurs through the properties of the material constituting the stent. Examples of intravascular stents can be found in U.S. Pat. No. 5,292,331 to Boneau; U.S. Pat. No. 4,580,568 to Gianturco; U.S. Pat. No. 4,856,516 to Hillstead; U.S. Pat. No. 5,092,877 to Pinchuk; and U.S. Pat. No. 5,514,154 to Lau et al.

One problem with some prior art stents, especially those of the expandable type, is that they are often stiff and inflexible. Often, the expandable type stents are formed from stainless steel alloys and are constructed so that they are expanded beyond their elastic limit. Such stents are permanently deformed beyond their elastic limits in order to hold open a body lumen and to maintain the patency of the body lumen. By the same token, since the material is stressed beyond its elastic limit into the plastic region, the material becomes stiff and inflexible.

There are several commercially available stents that are widely used and generally implanted in the coronary arteries after a PTCA procedure. Another class of stents is implanted in vessels that are closer to the surface of the body, such as in the carotid arteries in the neck or in peripheral arteries and veins in the leg. Because these stents are so close to the surface of the body, they are particularly vulnerable to impact forces that can partially or completely collapse the stent and thereby block fluid flow in the vessel. Since these prior art stents are plastically deformed, once collapsed or crushed, they remain collapsed, permanently blocking the vessel. Thus, the prior art stents can pose an undesirable condition to the patient.

Other forces can impact the prior art stents and cause similar partial or total vessel occlusion. Under certain conditions, muscle contractions might cause the prior art stents to partially or totally collapse and to restrict blood flow in the vessel in which they are implanted.

Such important applications as mentioned above have prompted stent designers to use superelastic or shape memory alloys in their stent to exploit the materials'properties. An example of such shape memory alloy stents is disclosed in, for example, European Patent Application Publication No. EP0873734A2, entitled "Shape Memory Alloy Stent." This publication suggests a stent for use in a lumen in a human or animal body having a generally tubular body formed from a shape memory alloy which has been treated so that it exhibits enhanced elastic properties.

The evolution of superelastic and shape memory alloy stents progressed to use of ternary elements in combination with nickel-titanium alloys to obtain specific material properties. Use of a ternary element in a superelastic stent is shown in, for example, U.S. Pat. No. 5,907,893 to Zadno-Azizi et al. As a general proposition, there have been attempts at adding a ternary element to nickel-titanium alloys as disclosed in, for instance, U.S. Pat. No. 5,885,381 to Mitose et al.

Another goal has been to design stents that are capable of easy passage through tortuous anatomies such as those found in a coronary artery. One design entails a nitinol stent having a multiplicity of undulating longitudinal struts that can readily change their lengths in the longitudinal direction so as to provide increased longitudinal flexibility for the stent. An example of such a construction is shown in U.S. Pat. No. 5,879,370 to Fischell et al.

Designing stents for extremely curved and highly tortuous anatomies requires a stent that can bend sufficiently without the struts kinking. To address this kinking problem, one concept is to construct a tubular stent with helically-arranged undulating members having a plurality of helical turns. Linking members formed by rings are laced or interwoven between the undulations in adjacent turns of the helical undulating members. U.S. Pat. No. 6,042,605 to Martin et al. discloses such a construction. The linked undulating elements facilitate bending of the stent.

The foregoing stent designs address the problems with delivering a straight length stent into a tortuous anatomy. These designs, do not, however, address the problems with deploying a straight length stent in an extremely curved vessel. Indeed, when a straight length stent is deployed in a curved vessel, the stent tends to straighten the curved vessel to follow the form of the stent. It is believed that the straightening forces of the stent is damaging to the health of the vessel, may create emboli, and may generate intimal flaps that promote restenosis.

One possible solution suggests assembling a composite stent piecemeal at the curved vessel delivery site by using short modular sections. This approach is disclosed in U.S. Pat. No. 5,824,037 to Fogarty et al. In this design, modular sections of the prosthesis may be selectively combined to form a composite prosthesis having characteristics that are tailored to the specific requirements of the patient. Each prosthetic module includes one or more standard interface ends for engaging another module, the module interface typically having ends that overlap and/or lock within a predetermined axial range. Selection of the appropriate prosthetic modules and the flexibility of the interface overlap range provide a custom fit intraluminal prosthesis tailored to the individual patient's needs. The module sections may include bends, although the modules are individually introduced into a lumen system of a patient's body so that the composite prosthesis is assembled in situ. Generally, the prosthetic body modules have a variety of selectable body links, bends, and taper characteristics.

Although the foregoing conventional stent designs begin to address the problems with deploying a straight stent in an extremely tortuous or curved anatomy, there is, however, still a need for a superelastic stent that is specifically intended for use in tortuous anatomies. The present invention satisfies this need.

SUMMARY OF THE INVENTION

The present invention is directed to a stent for use in a curved body lumen, comprising a cylindrically-shaped stent including a superelastic alloy, wherein the stent has a unitary construction, and has a length that is greater than a diameter. The superelastic alloy has a low temperature phase that induces a first shape to the stent, and a high temperature phase that induces a second shape with a bend along the length of the stent, and wherein the bend substantially conforms to the curved body lumen.

In a preferred embodiment, the high temperature phase corresponds to an austenitic phase and the low temperature phase corresponds to a martensitic phase. Also, preferably, the superelastic alloy is a nickel-titanium composite that may optionally include a ternary element selected from the group of elements consisting of palladium, platinum, chromium, iron, cobalt, vanadium, manganese, boron, copper, aluminum, tungsten, tantalum, or zirconium.

In a preferred embodiment, a nickel-titanium or nitinol self-expanding stent can be heat set with various degrees of arch or curvature along its length to accommodate a curved or tortuous vessel anatomy. Therefore, when the stent is deployed in a patient's body at above the superelastic alloys phase transformation temperature, the stent reverts to its austenitic phase. In this state, the present invention stent assumes its expanded shape with a bend, wherein the bend was heat set to match or approximate the curvature of the curved vessel. A taper may also be heat set into the stent so that it assumes a tapered and curved profile upon expansion.

Prior art self-expanding nitinol stents that have a straight length, when deployed, exert a continuous radial force on the vessel wall at the deployment site. These prior art stents have a tendency to straighten the lumen regardless of the lumen's natural curvature. In contrast, the present invention stent with a heat set curve along its length does not have the same tendency to straighten when inside the curved vessel. Accordingly, trauma to the vessel is minimized and damage to the intima is diminished. Furthermore, the longitudinal bend or bends that are heat set into the present invention stent can vary in both angle and radius of curvature. In various alternative embodiments, the present invention when in the high temperature state may include a curved length that bends in two dimensions, or may have a bend of greater than 90 degrees, or may have compound curves, or any combination of the foregoing.

In the preferred embodiment, the present invention stent is unitary, being fashioned from a single piece of material. The present invention stent is also preferably of sufficient length to have an aspect ratio in which the length is greater than its diameter. This ensures that the stent does not tip within the lumen, and minimizes the chance that the stent may migrate and cause an embolism.

The present invention may optionally include radiopaque markers that assist the physician in proper orientation of the curved stent at the deployment site. In particular, the radiopaque marker may include directional indicia that can be seen in a fluoroscope or by X-ray that help the physician recognize the orientation of the stent. Moreover, the present invention may be delivered by any delivery system and method presently known in the art.

The present invention further contemplates a delivery system having a radiopaque pattern disposed on the delivery sheath wherein the pattern provides an indication to the physician as to the bend in the self-expanding stent when deployed inside the curved body lumen. By using the radiopaque marker as a point of reference, it is possible for the physician to manipulate the delivery system and to deploy the self-expanding stent such that upon expansion of the self-expanding stent, the bend in the stent corresponds to the curvature in the lumen.

In a preferred embodiment, the radiopaque pattern includes a tubular shape arrangement of rings interconnected by a spine. Thus, as the stent delivery system is rotated within a curved anatomy, one radial along the length of the stent delivery system exhibits constant radiopacity and the location exactly 180 degrees opposed has variable radiopacity as it is bent from concave to convex. When this location has minimum radiopacity in a convex bend (and the spine assumes a concave bend), the stent delivery system is correctly oriented, and the curve of the self-expanding stent closely matches the curve of the anatomy.

Other features and advantages of the present invention will become more apparent from the following detailed description of the invention when taken in conjunction with the accompanying exemplary drawings.

BRIEF DESCRIPTION OF THE DRAWINGS

FIG. 4f specifically illustrates a bend and a taper in the stent.

FIGS. 5a–5b are cross-sectional views of an exemplary embodiment stent delivery system for use with the present invention showing deployment of a curved self-expanding stent.

DETAILED DESCRIPTION OF THE PREFERRED EMBODIMENTS

The present invention in a preferred embodiment is directed to a stent and delivery system for use in a curved body lumen. The stent is preferably made of a superelastic alloy in which the material properties are exploited to achieve a specific curved shape for the stent when deployed.

The stents of the present invention can have virtually any configuration that is compatible with the body lumen in which they are implanted. The radial force of the stent should be configured so that there is a substantial amount of open area once the stent has been deployed. Preferably the open area to metal ratio is at least 400 percent. The stent also should be configured so that dissections or flaps in the body lumen wall are covered and tacked up by the stent.

Figure 1:
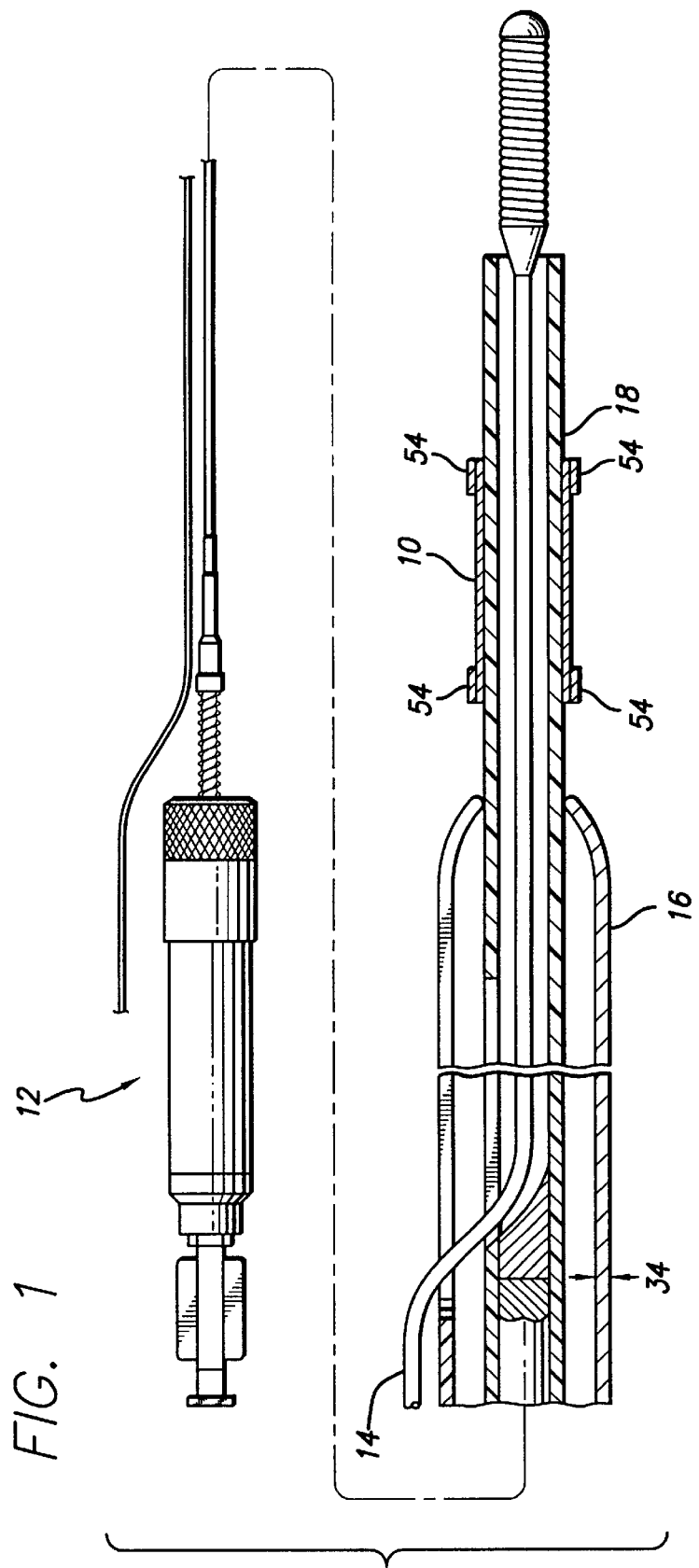
FIG. 1 is a partial cross-sectional view of a stent delivery system for use with the present invention.
Figure 2:
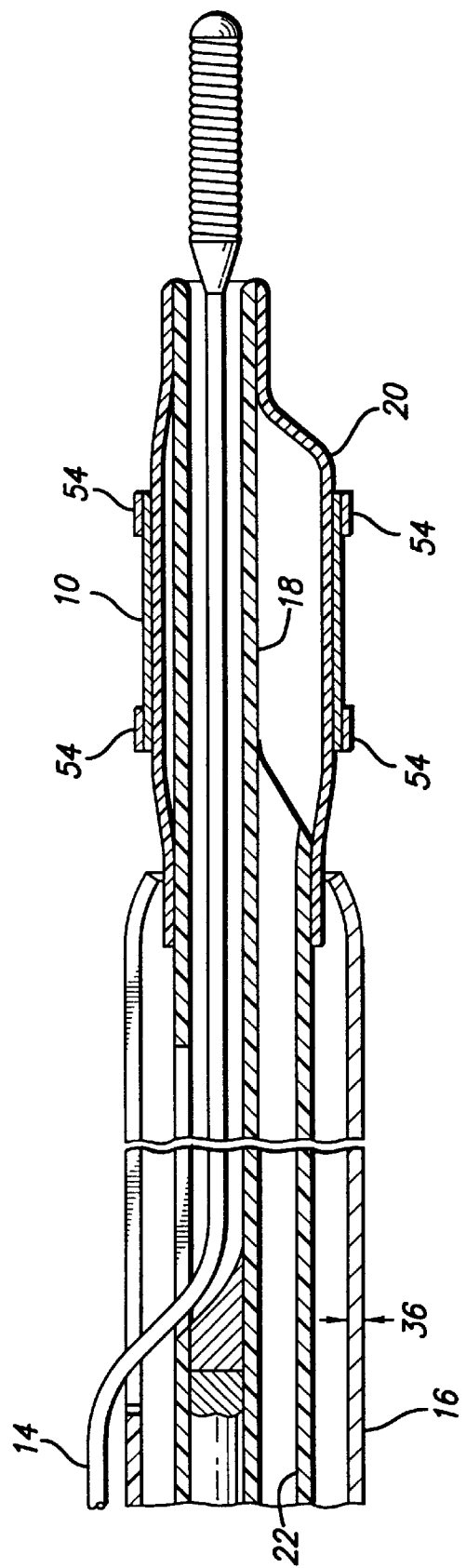
FIG. 2 shows, in a cross-sectional view, the stent delivery system of FIG. 1 with an optional expandable balloon.
Figure 3:
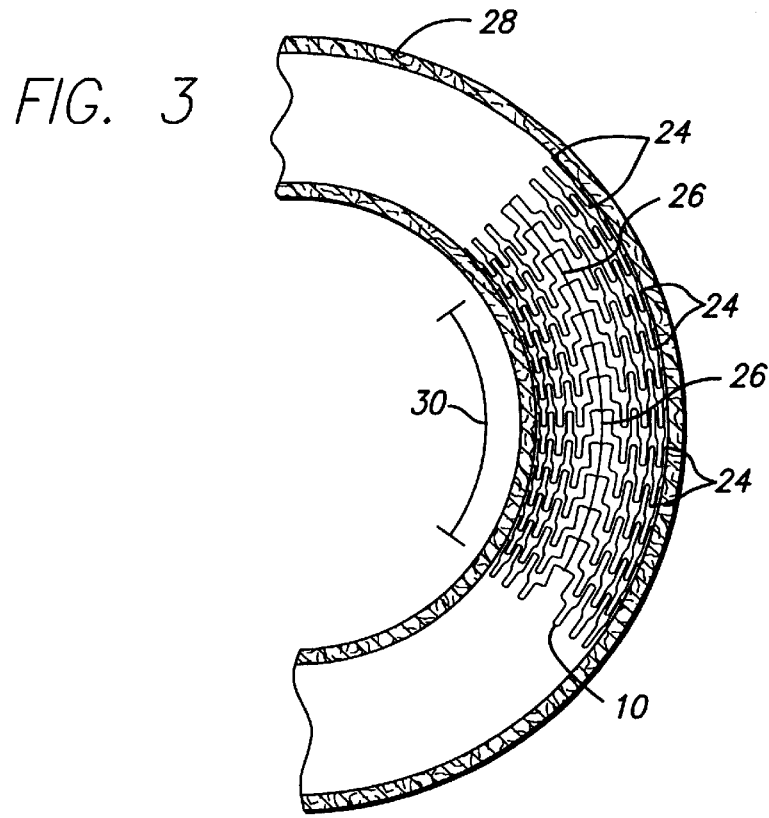
FIG. 3 is a cross-sectional view of a curved vessel exposing a deployed stent of the present invention.

Referring to FIGS. 1, 2 and 3, in a preferred embodiment, a stent 10 of the present invention is formed partially or completely of alloys such as nitinol (NiTi) which have superelastic (SE) characteristics. The stent 10 is somewhat similar to the stent disclosed in, for example, U.S. Pat. No. 5,569,295, "Expandable Stents and Method for Making Same," issued to Lam on Oct. 29, 1996, which is incorporated herein by reference in its entirety.

The strut configuration of the stent 10 shown in FIG. 3 is just one example of many strut configurations that are contemplated by the present invention. In this embodiment, the stent 10 has a plurality of radially expandable cylindrical elements 24 disposed generally coaxially to achieve a tubular form. This imaginary tube has a flexible but straight length prior to deployment as shown in profile in FIGS. 1 and 2. In the deployed state in FIG. 3, the tubular form is curved along its length to follow the curvature of the artery or vessel 28.

The radially expandable cylindrical elements 24 are interconnected by spines 26 disposed between adjacent cylindrical elements 24 and that generally extend the length of the stent 10. The shape of the struts are designed so they can preferably be tightly packed. This means that the serpentine shaped struts have extended portions in one cylindrical element 24 that intrude into a complementary space within the circumference of an adjacent cylindrical element 24.

Furthermore, the stent 10 is unitary, meaning that it is fashioned from a single piece of material. For example, the stent 10 is cut to length from stock nitinol or like material tubing. The tubing is then laser cut to form the strut pattern. Through this process, the present invention unitary stent construction avoids the process variances and deficiencies of welded or mechanically linked together stents. Certainly engineering properties and dimensional tolerances can be more easily controlled with a one-piece stent as compared to a stent pieced together from component parts.

As mentioned above, an exemplary stent of the present invention includes a superelastic material. The term "superelastic" refers to alloys having superelastic properties that include at least two phases: a martensitic phase, which has a relatively low tensile strength and which is stable at relatively low temperatures and an austenitic phase, which has a relatively high tensile strength and which is stable at temperatures higher than the martensitic phase. Superelastic characteristics generally allow the metal stent to be deformed by collapsing and deforming the stent and creating stress which causes the NiTi to change to the martensitic phase. The stent is restrained in the deformed condition within a delivery system to facilitate the insertion into a patient's body, with such deformation causing the phase transformation. Once within the body lumen, the restraint on the stent is removed, thereby reducing the stress therein so that the superelastic stent can return to its original undeformed shape by the transformation back to the austenitic phase.

More precisely, when stress is applied to a specimen of a metal such as nitinol exhibiting superelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase. As the phase transformation progresses, the alloy undergoes significant increases in strain with little or no corresponding increases in stress. The strain increases while the stress remains essentially constant until the transformation of the austenitic phase to the martensitic phase is complete. Thereafter, further increase in stress is necessary to cause further deformation. The martensitic metal first yields elastically upon the application of additional stress and then plastically with permanent residual deformation.

If the load on the specimen is removed before any permanent deformation has occurred, the martensite specimen elastically recovers and transforms back to the austenitic phase. The reduction in stress first causes a decrease in strain. As stress reduction reaches the level at which the martensitic phase transforms back into the austenitic phase, the stress level in the specimen remains essentially constant (but less than the constant stress level at which the austenitic crystalline structure transforms to the martensitic crystalline structure until the transformation back to the austenitic phase is complete); i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity.

The prior art makes reference to the use of metal alloys having superelastic characteristics in medical devices which are intended to be inserted or otherwise used within a patient's body. See, for example, U.S. Pat. No. 4,665,905 to Jervis and U.S. Pat. No. 4,925,445 to Sakamoto et al.

Returning to FIG. 1, the graphic illustrates, in a partial cross-sectional view, a rapid exchange stent delivery system that includes a manipulating device 12, a guide wire 14, a delivery sheath 16, and an intravascular catheter 18. The stent 10 is usually held underneath the delivery sheath 16, but FIG. 1 illustrates the system with the sheath 16 retracted.

This simplified illustration of the delivery system is just one example of many that may be used with the present invention. More details of a delivery system specifically for use with a self-expanding stent may be found in, for example, U.S. Pat. No. 6,077,295, "Self-Expanding Stent Delivery System," issued to Limon et al. on Jun. 20, 2000, which is incorporated herein by reference. Other delivery systems such as an over-the-wire delivery system may be used without departing from the scope of the instant invention.

FIG. 2 depicts in a partial cross-sectional view a variation of the delivery system of FIG. 1, which variation includes an optional expandable balloon 20 and an optional balloon inflation lumen 22. The stent 10 is disposed over the expandable balloon 20, and the entire assembly is kept underneath the delivery sheath 16 until the moment the stent 10 is deployed. Again, this illustration shows the delivery sheath 16 in the retracted condition.

The present invention stent 10 is preferably formed from a superelastic material such as NiTi and undergoes an isothermal transformation when stressed. The stent is first compressed to a delivery diameter, thereby creating stress in the NiTi alloy so that the NiTi is in a martensitic state having relatively low tensile strength. Alternatively, the present invention stent 10 may be chilled to its low temperature martensitic state and deformed into its small delivery diameter. In either case, while still in the martensitic phase, the stent 10 is mounted onto a catheter by known methods such as adhesives, or other restraining means. By virtue of the superelastic properties, the stent 10 when mounted within the delivery sheath 16 tends to spring back to a larger diameter, and pushes radially outward against the inside diameter of the sheath 16 when held therein.

In its delivery diameter, the overall diameter of the stent and catheter are less than the inside diameter of an artery 28 or the vessel in which they are inserted. After the stent 10 is inserted into the artery or other vessel, the stress exerted by the stent 10 may be released by withdrawing the delivery sheath 16 in a proximal direction, whereupon the stent 10 immediately expands and returns to its original, undeformed shape by transforming back to the more stable austenitic phase. If the expandable balloon 20 of FIG. 2 is used, the stent 10 may be further expanded by inflation of the expandable balloon 20 via the balloon inflation lumen 22 by known methods.

To exploit the properties of superelastic alloys, the present invention stent 10 can be heat set with various degrees of curvature along its length to conform to the curvatures of any number of patients' vasculatures. A conventional, superelastic stent that is heat set straight along its length, when deployed, exerts a continuous radial force and attempts to straighten the lumen regardless of the lumen's original anatomy or curvature. Therefore, in some cases, it may be better to deploy a self-expanding stent that more closely matches the original curvature of the lumen to avoid these stresses upon the vessel. The arch shape that is heat set into the present invention superelastic stent 10 can vary in both total angle and radius of curvature.

For example, FIG. 3 is a partial cross-sectional view of a vessel 28 having a particular curvature or bend 30. The superelastic stent 10 has been deployed and is illustrated in its high temperature, expanded state. In other words, the stent 10 is in its austenitic phase in which the stent 10 assumes a shape having a curvature or bend along its length that conforms and matches the curvature 30 of the vessel 28. In contrast, prior to reaching the deployment site as depicted in FIG. 3, the stent 10 remains in its low temperature or martensitic state. In this state, the stent 10 is held inside the delivery sheath 16 and has a shape that does not include the bend shown in FIG. 3. In this martensitic state, the present invention stent 10 is fairly pliable and follows the flexures of the delivery system along the tortuous anatomy of the patient.

As seen in FIG. 3, the length of the stent 10 can be as long as needed to perform its scaffolding function along the diseased portion of the vessel 28. In the exemplary embodiment, the diameter of stent 10 is preferably smaller than the length of the stent 10 because this aspect ratio ensures that the stent does not tip and migrate downstream causing an embolism. In its austenitic phase, the heat set curve along the length of the stent 10 conforms closely to the natural bend 30 of the vessel 28. Ideally, this bend should follow the curvature 30 of the vessel 28 fairly closely. Therefore, the present invention contemplates a variety of curvatures that may be heat set into the length of the superelastic stent 10 to match the unique vasculatures in different patients.

Figure 4A:
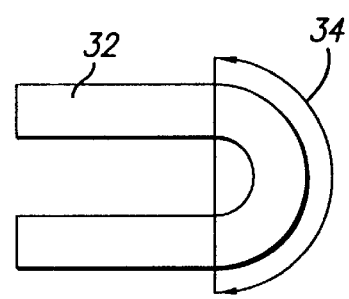
FIGS. 4a–4f are schematic drawings of exemplary embodiments of curves and bends of the present invention stent.
Figure 4B:
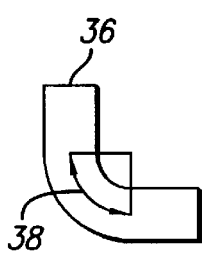
Figure 4C:
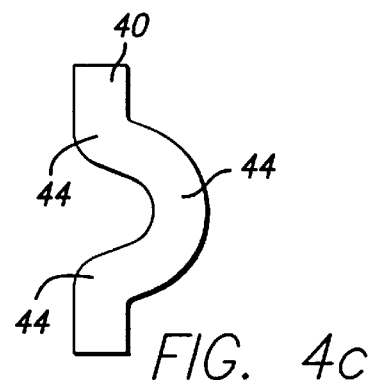
Figure 4D:
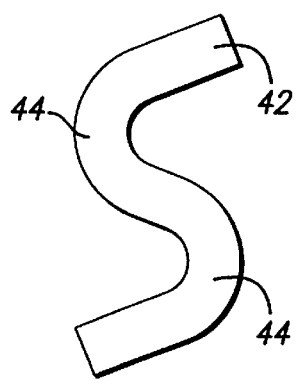
Figure 4E:
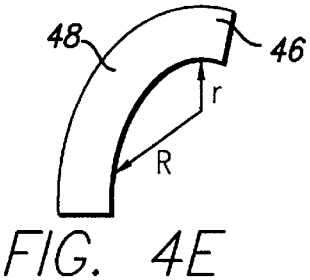
Figure 4F:
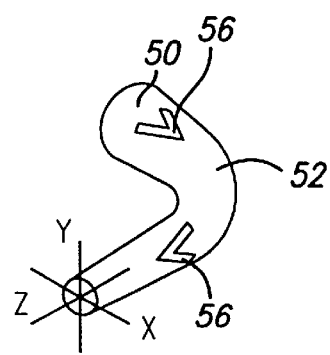

FIGS. 4a–4f provide schematic views of the present invention stent in its high temperature phase with a variety of induced bends and curves along the length of the stent. More precisely, FIG. 4a illustrates a stent 32 having a 180 degree bend 34 along its length. In FIG. 4b, stent 36 has a 90 degree bend 38 along its length. FIGS. 4c and 4d illustrate stents 40 and 42 having multiple bends 44. FIG. 4e illustrates a stent 46 having a compound curve 48 in which the compound curve has at least two radii of curvature, $r$ and $R$. FIG. 4f illustrates yet another alternative embodiment stent 50 having a bend 52 that extends into three dimensions. In particular, the bend 52 occurs along plane x-y, along plane x-z and along plane y-z. Any and all combinations of the foregoing and other bends and curves known in the art are also contemplated.

The perspective view of FIG. 4f further illustrates a taper along the length of the stent 50. The tapered profile is created by having a small diameter at the end of stent 50 facing out of the page and a large diameter at the end of stent 50 facing into the page. The tapered profile is set into the stent 50 by applying the same processes as for imparting the bend 52, described elsewhere. Although the taper illustrated in FIG. 4f extends the entire length of the stent 50, it is understood that the taper may also assume a stepped configuration, or the taper can be formed into just one end of the stent.

The delivery system for the present invention curved, self-expanding stent 10 can be as straight and as flexible as a conventional delivery system for a straight, self-expanding stent. Upon deployment, the superelastic stent assumes its heat set curved and expanded shape shown in FIG. 3. The delivery system optionally includes some type of radiopaque marking to indicate the orientation of the stent 10 prior to its deployment, thus allowing the physician to rotationally position the stent 10 such that its curvature or bend matches the curvature or bend of the vessel. The delivery system at its proximal end, perhaps on the handle, may display markings to assist in physician stent orientation and placement.

Optional radiopaque bands or markers 54 shown in FIGS. 1 and 2 may be included on the stent 10 to assist the physician in orienting and positioning the stent within the curved vessel 28. The radiopaque markers 54 may be in the form of bands as shown in FIGS. 1 and 2, they may be coatings, they may be embedded within the stent, or they may be simply thicker or wider struts that appear more distinctly on a fluoroscope. Also, selecting more radiopaque materials to alloy with the base material is another solution.

Preferably, the radiopaque markers 54 have some unique directional indicia to assist the physician in recognizing the orientation of the stent when viewed in a two-dimensional screen such as a fluoroscope often found in a cath lab.

To illustrate, in an alternative embodiment shown in FIG. 4f, curved stent 50 has directional radiopaque markers 56 in the form of chevrons that assist the physician in recognizing the orientation of this curved stent inside the patient's vasculature. Although as shown in FIG. 4f the stent 50 is in its expanded, deployed state, the chevron markers 56 nevertheless are effective in the compressed delivery diameter to help with placement and orientation.

The present invention superelastic alloy is preferably formed from a nickel-titanium composition known in the art. The process to heat set the curved shape of the present invention stent is performed by mounting the stent on a mandrel having the desired curvature, taper, etc., and raising the temperature of the stent to a point above the austenitic finish ($A_f$) of the material. The process details for heat setting a nickel-titanium alloy is well known in the art. After the heat set procedure, the stent 10 is removed from the mandrel and returned to room temperature. In the exemplary embodiment, the nitinol alloy has a transition temperature that is below human body temperature, and preferably below room temperature.

The superelastic alloy of the present invention may alternatively be formed from a composition consisting essentially of about 30 to about 52 percent titanium and the balance nickel and up to 10 percent of one or more additional ternary alloying elements. Such ternary alloying elements may be selected from the group consisting of palladium, platinum, chromium, iron, cobalt, vanadium, manganese, boron, copper, aluminum, tungsten, tantalum, or zirconium. In particular, the ternary element may optionally be up to 10 percent each of iron, cobalt, platinum, palladium, or chromium, and up to about 10 percent copper and vanadium. As used herein, all references to percent composition are atomic percent unless otherwise noted.

In another preferred embodiment, a NiTi stent with SME (shape memory effect) is heat-treated at approximately 500 degrees C. The stent is mechanically deformed into a first, smaller diameter for mounting on a catheter delivery system, such as the delivery system of FIG. 2, that includes the expandable balloon 20 and the balloon inflation lumen 22. After the stent has been expanded by the balloon and deployed against arterial wall 29 of artery 28, 45 degrees C. heat is applied causing the stent to return to its fully expanded, curved length and to contact the curved arterial wall of the artery. The application of 45 degrees C. of heat is compatible with most applications in the human body, but it is not to be limited to this temperature as higher or lower temperatures are contemplated without departing from the invention. The 45 degrees C. temperature can be achieved in a conventional manner well known in the art such as by warm saline injected into the delivery catheter and balloon.

The shape memory characteristics allow the devices to be deformed to facilitate their insertion into a body lumen or cavity and then to be heated within the body so that the device returns to its original, curved-length shape. Again, alloys having shape memory characterisitcs generally have at least two phases: a martensitic phase, which has a relatively low tensile strength and which is stable at relatively low temperatures, and an austenitic phase, which has a relatively high tensile strength and which is stable at temperatures higher than the martensitic phase.

Shape memory characteristics are imparted to the alloy by heating the metal to a temperature above which the transformation from the martensitic phase to the austenitic phase is complete; i.e., a temperature above which the austenitic phase is stable ($A_f$). The curved shape of the metal during this heat treatment is the curved shape "remembered." The heat-treated metal is cooled to a temperature at which the martensitic phase is stable, causing the austenitic phase to transform to the martensitic phase. The metal in the martensitic phase is then plastically deformed, e.g., to facilitate the entry thereof into a patient's body via a delivery system. Subsequent heating of the deformed martensitic phase to a temperature above the martensite to austenite transformation temperature causes the deformed martensitic phase to transform to the austenitic phase. During this phase transformation the metal reverts back to its original curved shape.

The recovery or transition temperature may be altered by making minor variations in the composition of the metal and in processing the material. In developing the correct composition, biological temperature compatibility must be determined in order to select the correct transition temperature. In other words, when the stent is heated, it must not be so hot that it is incompatible with the surrounding body tissue. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," *Scientific American*, Vol. 281, pp. 74–82 (November 1979).

Shape memory alloys undergo a transition between an austenitic state and a martensitic state at certain temperatures. When they are deformed while in the martensitic state they retain this deformation as long as they are retained in this state, but revert to their original configuration when they are heated to a transition temperature, at which time they transform to their austenitic state. The temperatures at which these transitions occur are affected by the nature of the alloy and the condition of the material. Nickel-titanium-based alloys (NiTi), wherein the transition temperature is slightly lower than body temperature, are preferred for this embodiment of the present invention. It is desirable to have the transition temperature set at just below body temperature to enable a rapid transition from the martensitic state to the austenitic state when the stent is implanted in a body lumen.

Turning again to FIGS. 2 and 3, the stent 10 is formed from a shape memory alloy, such as NiTi discussed above. When positioned at the delivery site within the vessel, the protective sheath 16 is retracted to expose the stent 10. The stent 10 then immediately expands due to contact with the higher temperature within artery 28 as described above for devices made from shape memory alloys. The stent 10 assumes its curved shape in the austenitic state and its curved shape closely conforms to the curvature 30 of the artery 28. After the stent 10 is deployed at the curved artery 28, the expandable balloon 20 is inflated via the balloon inflation lumen 22 by conventional means so that the stent 10 expands radially outward. The balloon 20 may optionally be curved (not shown) when inflated to follow the natural curvature 30 of the artery 28. The bend in the inflated balloon also avoids straightening out the curved, expanded stent.

FIGS. 5a and 5b are cross-sectional views of a preferred embodiment of the present invention stent and delivery system. Specifically, FIGS. 5a and 5b show the devices in a state prior to deployment of the curved stent in the curved lumen, and post deployment of the curved stent in the lumen, respectively. In the exemplary embodiment shown, an over-the-wire catheter 62 has a guide wire lumen 64 that extends through the catheter 62 and receives a guide wire 68 therein.

Generally speaking, in order to implant a self-expanding stent 70, the guide wire 68 is advanced through a patient's body lumen to a stenosed region 72. Typically, the guide wire 68 extends past the stenosed region 72. Next, a distal end 74 of the over-the-wire catheter 62 is threaded over the proximal end of the guide wire that is outside the patient (not shown) and the catheter 62 is advanced along the guide wire 68 until the distal end 74 of the catheter 62 is positioned within the stenosed region 72.

An outer member 76, sometimes referred to as a delivery sheath, is elastic and maintains a compressive force over the self-expanding stent 70. As a result, the compressed self-expanding stent maintains a small profile during delivery to the stenosed region 72.

As depicted in FIG. 5b, the self-expanding stent 70 is deployed in the stenosed region 72 by moving the outer member 76 in a proximal direction while simultaneously moving an inner member 78 in a distal direction. Optionally, the inner member 78 can be maintained stationary while the outer member 76 is moved in the distal direction to expose the self-expanding stent 70 thereby deploying the stent 70 at the stenosed region 72.

The stent 70 cannot slide or move axially on the outer surface 80, because the open lattice structure of the stent 70 engages a matrix of surface contours 82. As portions of the self-expanding stent 70 are no longer contained by the outer member 76, those portions expand radially outward into contact with the vessel wall 60 in the area of the stenosed region 72. When fully deployed and implanted, as shown in FIG. 5b, the stent 70 supports and holds open the stenosed region 72 so that blood flow is not restricted. The surface contours 82 do not inhibit the stent 70 from self-expanding radially outward; they only impede axial movement of the stent 70, which improves the precision of the apposition of the stent relative to the stenosed region 72.

With certain self-expanding stents, there is a tendency of the stent to shorten somewhat when it expands. When the stent shortening occurs, the physician may find that the stent has been improperly placed in the stenosed region if the effects of the shortening have not been taken into consideration. Accordingly, it may be necessary to move the inner member 78 distally in order to compensate for the stent shortening upon expansion of the stent. It is also possible due to stent design that the self-expanding stent does not appreciably shorten upon expansion. If this is the case, it is then unnecessary to move the inner member 78 distally while simultaneously moving the outer member 76 proximally in order to release the self-expanding stent 70 in the body lumen. With a stent configuration that does not appreciably shorten during expansion, the outer member 76 is moved proximally while the inner member 78 remains stationary as the self-expanding stent 70 expands radially outwardly into contact with the vessel wall 60. After the stent 70 is implanted and contacts the stenosed region 72, the over-the-wire catheter 62 is withdrawn from the patient's vasculature, completing the procedure.

The relative movement between the inner member 78 and the outer member 76 is accomplished by manipulation of the control handles 84, 86. The control handles 84, 86 can take the form of a thumb-switch, a rotating-screw, or a ratcheting arrangement, or the like. Such control handle mechanisms are well known in the art. The control handles 82,84 are located at the proximal end 88 of the catheter 62 for convenient access and manipulation by the physician. The foregoing delivery system is further described in detail in U.S. Pat. No. 6,077,295 to Limon et al., whose entire contents are hereby incorporated by reference.

As shown in FIGS. 5a and 5b, the vessel wall 60 has a bend 90. It is therefore important that the bend in the self-expanding stent 70 closely follows the vessel bend 90 upon deployment of the stent. Otherwise, the bias in the expanded stent 70 with its bend improperly aligned with the bend 90 in the vessel may impart trauma to the stenosed region 72 due to the misfit. It is thus useful for the physician to know beforehand the location and direction of the bend in the stent 70 prior to deployment such that the stent bend can be matched to the bend 90 in the vessel wall 60.

Still in the drawings, FIGS. 5a and 5b show the distal end 74 of the catheter 62 optionally embedded with a radiopaque marker pattern 92. This exemplary embodiment radiopaque marker pattern 92 is illustrated in a top plan view, side elevational view, and end view in FIGS. 6a, 6b, and 6c, respectively. The radiopaque marker pattern 92 has a spine 94 interconnecting a plurality of rings 96 that are aligned coaxially to generally form a tubular shape. The cross-sectional area of the rings 96 may be a rectangle as shown in the figures or can be any other of a variety of shapes. Likewise, the cross-sectional shape of the spine 94 is shown to be a circular shape, but other shapes are contemplated.

Figure 6A:
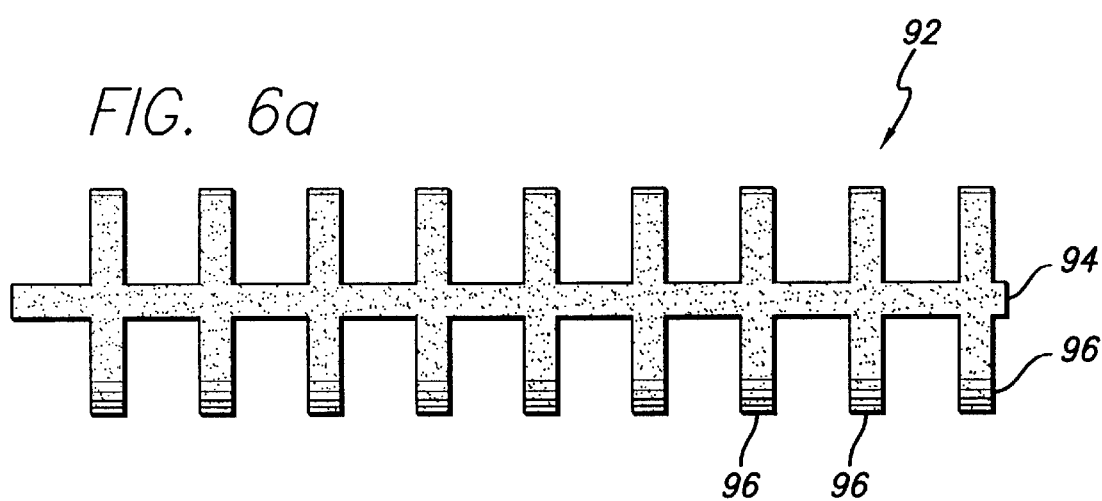
FIGS. 6a–6c are a top plan view, a side elevational view, and an end view, respectively, of a preferred embodiment radiopaque pattern of the present invention.
Figure 6B:
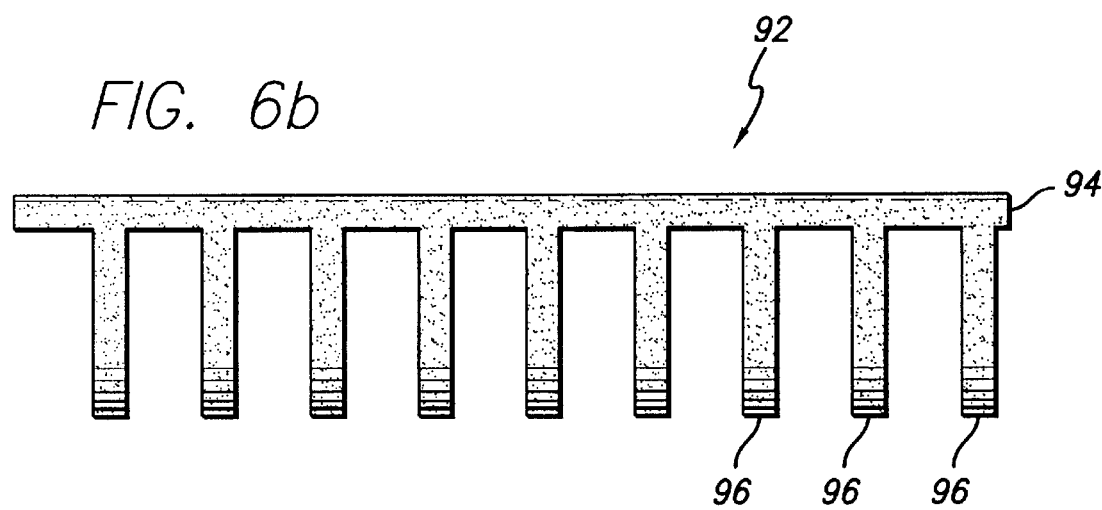
Figure 6C:
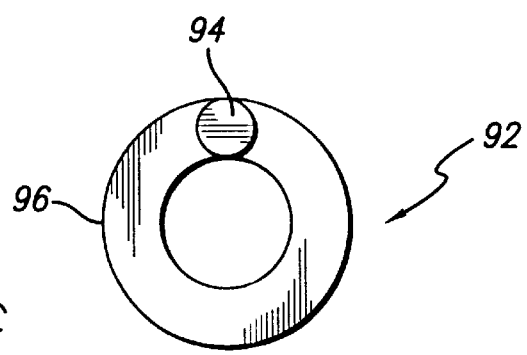

The illustrations of FIGS. 6a–6c depict the radiopaque marker pattern 92 in its undistorted condition, while the radiopaque marker pattern 92 is shown in FIGS. 5a and 5b in first a bent condition and then in a straight condition, respectively. The bent state of the radiopaque marker pattern 92 in FIG. 5a occurs when the spine 94 is rotationally and axially aligned with the bend 90 in the curved vessel wall 60. The bent state of the radiopaque marker pattern 92 is discernible by a physician using a fluoroscope or similar viewing device.

The spine 94 presents more radiopaque mass and generates a stronger image on the fluoroscope than the spaced apart rings 96. Therefore, if the heat set bend in the self-expanding stent 70 is oriented relative to the location of the spine 94 when contained inside the outer member 76, the physician is insured that when deployed, the bend in the stent 70 will closely match the bend 90 in the vessel wall 60. If the alignment is not acceptable, the physician can torque the catheter 62 prior to deployment until the image of the radiopaque marker pattern 92 and specifically the spine 94 is aligned with the curvature of the bend 90. Axial adjustments are also possible to align the distal and proximal ends of the stent with the stenosed region 72. When the rotational and axial alignments are achieved, the stent 70 can be deployed from the catheter 62.

FIGS. 6a–6c are various views of a preferred embodiment radiopaque marker pattern 92. In this embodiment, the rings 96 are evenly spaced apart, but asymmetrically located along the length of the spine 94 such that one of the spine extends farther from the end than the other. This asymmetrical pattern is helpful in recognizing the proximal versus distal ends of the stent when viewed in a fluoroscope, for example. The physician can then discern the direction the stent is facing. The direction the stent is facing is sometimes critical because the stent might include a taper and the physician would need to recognize whether the taper when deployed pointed distally or proximally.

The radiopaque marker pattern 92 shown in FIGS. 6a–6c can be, in various exemplary embodiments, constructed by laser cutting a tube of radiopaque material such as gold, platinum, tantalum, tungsten, barium, bismuth, or like materials. The identical pattern can be cut into the surface of the outer member 76 by use of plasma or laser etch, grinder erosion, or acid etch. The radiopaque marker pattern 92 is then embedded into the etched surface of the outer member 76 proximate to the distal end 74.

The radiopaque marker pattern 92 can be affixed to the etched surface of the outer member 76 by use of a glue. Alternatively, heat shrinking then cooling of the polymer material used for the outer member 76 expands the material to create a tight fit with the radiopaque marker pattern 92. Other methods known in the art can of course be used to attach the radiopaque marker pattern 92 to the outer member 76.

In the exemplary embodiment of the present invention depicted in FIGS. 5a, 5b, the inner member 78 and outer member 76 can be formed from polymeric materials such as latex, silicone, C-Flex, Tecoflex, polyurethane, polyethylene terephthalate (PET), polyethylene ethyl ketone (PEEK), polytetrafluorethylene (PTFE), nylon elastomer (PEBAX), and other materials known in the art. The surface contours 82 can be made in a preferred embodiment from polyurethane, elastomeric polyesters, and the like. In an alternative embodiment, the radiopaque marker pattern 92 can be formed from a polymeric material such as a polyether block amide (e.g. PEBAX) loaded with from approximately 60 percent to 90 percent of tungsten particles. The polymeric radiopaque marker pattern 92 can then be thermally bonded to the outer member 76. Because the outer member 76 and the radiopaque marker pattern 92 are both made of a polymeric material, both can expand or contract together. Other polymers used for markers as well as various radiopaque filler agents known in the art can be used together instead of the PEBAX material.

It is also possible in another alternative embodiment to provide the tubular structure of the radiopaque marker pattern 92 made of a radiopaque metal, and to shrink wrap the polymer outer member 76 over the radiopaque marker pattern 92. This process is known in the art. In yet another process, the polymeric outer member 76 is swaged or necked down to a thinner wall thickness so that the radiopaque marker pattern 92 can be glued thereon. Once released, the polymeric material returns to its original condition through elasticity and the marker pattern 92 is embedded therein. Once embedded, the radiopaque marker pattern 92 sits flush with the surface of the outer member 76. Optional grooves can be etched into the surface of the outer member 76 for even better seating as described earlier.

Installation of the curved stent 70 into the catheter 62 should preferably be coordinated with the orientation of the radiopaque marker pattern 92 in the outer member 76. In one exemplary embodiment, the bend in the self-expanding stent 70 should be rotationally aligned with the spine 94 of the radiopaque marker pattern 92 such that deployment of the self-expanding stent 70 causes the bend in the stent 70 to coincide with the location of the spine 94. Thus, if the physician aligns the spine 94 with the curved vessel wall 60, the physician is insured that the deployed stent 70 has a bend that matches the natural curve of the vessel wall 60. This orientation of the spine 94 in the radiopaque marker pattern 92 is illustrated in FIG. 5a wherein the spine 94 assumes a convex shape and the diametrically opposed side assumes a concave shape. Deployment of the stent 70 at this juncture promotes a good match between the bend in the stent 70 and the bend 90 in the vessel wall 60, as shown in FIG. 5b.

Alternatively, the spine 94 can be rotated 180 degrees out of phase from the orientation shown in FIG. 5a, insofar as the physician is first informed of how the self-expanding stent 70 will expand and the attitude of the bend in the stent upon deployment. In this alternative orientation, the spine 92 assumes a concave shape and the diametrically opposed side assumes a convex shape (not shown). When properly aligned, the bend in the stent 70 matches the bend 90 of the curved vessel wall 60.

Accordingly, the present invention stent delivery system contains a radiopaque marker that has one radiographic image along the inside radius of curvature when properly bent and a second radiographic image along the outside radius of curvature when properly bent. When these images are oriented correctly relative to the vascular anatomy, the self-expanding stent can be deployed. Thus, it is preferable to have a spine 24 to create sufficient radiopaque mass that is apparent on the fluoroscope and to omit this mass at 180 degrees out of phase from the spine, as seen in FIG. 6b. As the stent delivery system is rotated within the curved anatomy, one radial location along the length of the stent delivery system exhibits constant radiopacity; the location exactly 180 degrees opposed exhibits variable radiopacity as it is bent from concave to convex. When this location has minimum radiopacity, the stent delivery system is correctly oriented and the curve of the self-expanding stent agrees with the curve of the anatomy.

Of course, as shown in FIGS. 5a and 5b, the radiopaque marker pattern can be used 180 degrees out of phase from the orientation just described so that the convex portion of the curve is aligned with the spine 94 and the concave portion of the bend is aligned with an area 180 degrees out of phase with the spine 94. In such case, two solid radiopaque images appearing on the fluoroscope indicate that the bent stent is properly positioned in the curved anatomy and is ready for deployment.

Hence, one approach is to locate a large, radiopaque mass along the length of the radiopaque marker pattern 92 and to locate a small, radiopaque mass at 180 degrees out of phase from the large radiopaque mass. Following this objective, many alternative embodiment radiopaque marker patterns are contemplated aside from that shown in FIGS. 6a–6c.

While the present invention has been illustrated and described herein in terms of a superelastic stent and delivery system wherein the stent assumes a curved shape in its high temperature state, it is apparent to those skilled in the art that the present invention can be used in other instances. Other modifications and improvements may be made without departing from the scope of the present invention.

What is claimed is:

1. A self-expanding stent and delivery system for deploying the self-expanding stent in a curved body lumen, comprising:

a cylindrically-shaped self-expanding stent including a superelastic alloy, wherein the superelastic alloy includes a low temperature phase that induces a first shape to the stent, and a high temperature phase that isothermally induces a second shape with a bend along a length of the stent, wherein the bend substantially conforms to the curved body lumen;

a delivery sheath having a hollow interior at least partially containing the stent in the first shape;

a radiopaque pattern disposed in the delivery sheath, wherein the pattern includes a tubular shape affangement of rings interconnected by a spine;

wherein the stent is positioned in the delivery sheath so that the bend in the stent is oriented relative to the spine.

2. The self-expanding stent and delivery system of claim 1, wherein the radiopaque pattern includes a radiopaque material selected from the group consisting of gold, platinum, tantalum, tungsten, barium, or bismuth.

3. The self-expanding stent and delivery system of claim 1, wherein the high temperature corresponds to an austenitic phase and the low temperature corresponds to a martensitic phase.

4. The self-expanding stent and delivery system of claim 1, wherein the spine includes a circular cross-sectional shape.

5. The self-expanding stent and delivery system of claim 1, wherein the superelastic alloy includes nickel and titanium.

6. The self-expanding stent and delivery system of claim 1, wherein the second shape includes a tapered profile.

7. The self-expanding stent and delivery system of claim 1, wherein the superelastic alloy includes a nickel-titanium alloy with at least 30 to 52 percent titanium, and a ternary element that is selected from the group of elements consisting of palladium, platinum, chromium, iron, cobalt, vanadium, manganese, boron, copper, aluminum, tungsten, tantalum, or zirconium.

8. The self-expanding stent and delivery system of claim 7, wherein the superelastic alloy includes at least 38 percent nickel and up to 10 percent of the ternary element.

9. The self-expanding stent and delivery system of claim 1, wherein the radiopaque pattern is embedded to the delivery sheath.

10. A self-expanding stent and delivery system for deploying the self-expanding stent in a curved body lumen, comprising:

a cylindrically-shaped self-expanding stent including a superelastic alloy, wherein the superelastic alloy includes a low temperature phase that induces a first shape to the stent, and a high temperature phase that induces a second shape without application of heat and with at least one bend along a length of the stent, wherein the at least one bend substantially conforms to at least a curved section of the curved body lumen;

an elastic delivery sheath having a hollow interior at least partially restraining the stent in the first shape;

a flexible radiopaque pattern disposed in the delivery sheath, wherein the pattern includes a tubular shape arrangement of rings interconnected by a spine;

wherein the stent is held in the delivery sheath so that the bend in the stent is oriented relative to the spine.

11. The self-expanding stent and delivery system of claim 10, wherein the bend in the stent is aligned proximate to the spine when the stent is held inside the delivery sheath.

12. The self-expanding stent and delivery system of claim 10, wherein the bend in the stent is oriented approximately 180 degrees rotation from the spine when the stent is held inside the delivery sheath.

13. The self-expanding stent and delivery system of claim 10, wherein the second shape includes a taper along a length thereof.

14. The self-expanding stent and delivery system of claim 10, wherein the superelastic alloy includes nickel-titanium alloy having an austenitic phase above approximately 37 degrees C.

15. The self-expanding stent and delivery system of claim 10, wherein the delivery sheath includes a polymer and the radiopaque pattern is embedded in the polymer.

16. A process for deploying a self-expanding stent in a curved body lumen with a delivery system, comprising:

providing a cylindrically-shaped self-expanding stent including a superelastic alloy, wherein the superelastic alloy includes a low temperature phase that induces a first shape to the stent, and a high temperature phase that isothennally induces a second shape with a bend along a length of the stent, wherein the bend substantially conforms to the curved body lumen;

providing a delivery sheath having a hollow interior at least partially containing the stent in the first shape;

providing a radiopaque pattern in the delivery sheath, wherein the pattern includes a tubular shape arrangement of rings interconnected by a spine;

installing the stent in the first shape inside the delivery sheath;

positioning the stent in the delivery sheath so that the bend in the stent is oriented relative to the location of the spine.

17. The process for deploying a self-expanding stent in a curved body lumen of claim 16, wherein the process includes orienting the bend in the stent in approximate alignment with the spine.

18. The process for deploying a self-expanding stent in a curved body lumen of claim 16, wherein the process includes orienting the bend in the stent approximately 180 rotational degrees from the spine.

19. The process for deploying a self-expanding stent in a curved body lumen of claim 16, wherein the superelastic alloy includes a nickel-titanium alloy having a low temperature martensitic phase and a high temperature austenitic phase.

20. The process for deploying a self-expanding stent in a curved body lumen of claim 16, wherein the radiopaque strut pattern is fabricated from wire.

* * * * *